(12) United States Patent
Hirschl et al.

(10) Patent No.: US 10,166,046 B2
(45) Date of Patent: *Jan. 1, 2019

(54) IMPLANT FOR IMMOBILIZING CERVICAL VERTEBRAE

(71) Applicant: Life Spine, Inc., Huntley, IL (US)

(72) Inventors: Robert Hirschl, Clive, IA (US);
Michael S. Butler, St. Charles, IL (US); Daniel Predick, Chicago, IL (US); Madeline C. Wolters, Carol Stream, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/650,336

(22) Filed: Jul. 14, 2017

(65) Prior Publication Data

US 2017/0311990 A1    Nov. 2, 2017

Related U.S. Application Data

(63) Continuation of application No. 14/596,849, filed on Jan. 14, 2015, now Pat. No. 9,707,015.

(60) Provisional application No. 61/927,095, filed on Jan. 14, 2014.

(51) Int. Cl.
*A61B 17/70* (2006.01)

(52) U.S. Cl.
CPC ...... *A61B 17/7056* (2013.01); *A61B 17/7047* (2013.01); *A61B 17/7055* (2013.01)

(58) Field of Classification Search
CPC ............ A61B 17/7044; A61B 17/7047; A61B 17/7055; A61B 17/7056
See application file for complete search history.

(56) References Cited

U.S. PATENT DOCUMENTS

| | | |
|---|---|---|
| 5,142,953 A | 9/1992 | Lin |
| 5,217,497 A | 6/1993 | Mehdian |
| 5,667,526 A | 9/1997 | Levin |
| 5,688,272 A | 11/1997 | Montague et al. |
| 5,727,899 A | 3/1998 | Dobrovolny |
| 5,885,286 A | 3/1999 | Sherman et al. |

(Continued)

OTHER PUBLICATIONS

Written Opinion of the International Searching Authority for PCT Application No. PCT/US2008/069899, dated Sep. 8, 2008, 4 pages.

*Primary Examiner* — Jacqueline Johanas
(74) *Attorney, Agent, or Firm* — Foley & Lardner LLP

(57) ABSTRACT

A spinal implant for immobilizing the C1 vertebra with respect to the C2 vertebra of the spine provides controlled coupling between the C1 and C2 vertebrae, and includes a C1 component attachable to the C1 vertebra, two C2 components attachable to the C2 vertebra, and a transverse element. The C1 component has two wings each of which retains a rod holder that rotates and translate for capturing a C2 component rod. Each C2 component has a hook for connection with a side of the C2 vertebra lamina and a rod for attachment to one of the rod holders of the C1 component. Each C2 component receives and secures the transverse connector which holds position of the C2 components relative to one another. Each C2 component may include a plate configured for compression against the C2 vertebra spinous process, with each plate including spikes to aid in preventing construct migration.

20 Claims, 10 Drawing Sheets

(56) References Cited

U.S. PATENT DOCUMENTS

| | | | |
|---|---|---|---|
| 5,928,232 A * | 7/1999 | Howland | A61B 17/7001 606/276 |
| 5,947,966 A | 9/1999 | Drewry et al. | |
| 5,968,008 A | 10/1999 | Grams | |
| 6,017,306 A | 1/2000 | Bigliani et al. | |
| 6,096,039 A | 8/2000 | Stoltenberg et al. | |
| 6,110,173 A | 8/2000 | Thomas, Jr. | |
| 6,123,482 A | 9/2000 | Keller | |
| 6,238,396 B1 | 5/2001 | Lombardo | |
| 6,311,586 B1 | 11/2001 | Hirse | |
| 6,524,310 B1 | 2/2003 | Lombardo et al. | |
| 6,616,664 B2 | 9/2003 | Walulik et al. | |
| 6,709,435 B2 * | 3/2004 | Lin | A61B 17/7001 606/250 |
| 6,730,089 B2 | 5/2004 | Jackson | |
| 6,736,775 B2 | 5/2004 | Phillips | |
| 7,204,838 B2 | 4/2007 | Jackson | |
| 7,250,052 B2 | 7/2007 | Landry et al. | |
| 7,314,331 B1 | 1/2008 | Koros et al. | |
| 7,553,279 B1 | 6/2009 | Phillips et al. | |
| 7,618,443 B2 * | 11/2009 | Abdou | A61B 17/6433 606/267 |
| 7,666,210 B2 | 2/2010 | Franck et al. | |
| 7,744,632 B2 | 6/2010 | Usher | |
| 7,749,163 B2 | 7/2010 | Mulac et al. | |
| 7,837,714 B2 | 11/2010 | Drewry et al. | |
| 8,080,037 B2 | 12/2011 | Butler et al. | |
| 8,100,909 B2 | 1/2012 | Butler et al. | |
| 8,246,665 B2 | 8/2012 | Butler et al. | |
| 9,283,004 B2 * | 3/2016 | Hammer | A61B 17/7055 |
| 2003/0109881 A1 * | 6/2003 | Shirado | A61B 17/7022 606/330 |
| 2003/0114853 A1 | 6/2003 | Burgess et al. | |
| 2003/0187435 A1 * | 10/2003 | Lin | A61B 17/7001 606/250 |
| 2004/0267259 A1 * | 12/2004 | Mazda | A61B 17/707 606/250 |
| 2005/0113831 A1 | 5/2005 | Franck et al. | |
| 2005/0137602 A1 | 6/2005 | Assell et al. | |
| 2005/0228377 A1 | 10/2005 | Chao et al. | |
| 2006/0064093 A1 | 3/2006 | Thramann et al. | |
| 2006/0206114 A1 | 9/2006 | Ensign et al. | |
| 2006/0217710 A1 * | 9/2006 | Abdou | A61B 17/6433 606/54 |
| 2006/0271045 A1 | 11/2006 | Hubbard et al. | |
| 2007/0049932 A1 | 3/2007 | Richelsoph et al. | |
| 2007/0233090 A1 | 10/2007 | Naifeh et al. | |
| 2008/0086134 A1 | 4/2008 | Butler et al. | |
| 2008/0125781 A1 * | 5/2008 | Hoffman | A61B 17/7055 606/331 |
| 2008/0161856 A1 * | 7/2008 | Liu | A61B 17/7062 606/248 |
| 2008/0177314 A1 * | 7/2008 | Lemoine | A61B 17/7055 606/250 |
| 2009/0228046 A1 | 9/2009 | Garamszegi | |
| 2009/0254125 A1 | 10/2009 | Predick | |
| 2010/0036420 A1 | 2/2010 | Kalfas et al. | |
| 2010/0082067 A1 * | 4/2010 | Kondrashov | A61B 17/7044 606/264 |
| 2010/0094345 A1 | 4/2010 | Saidha et al. | |
| 2010/0222779 A1 * | 9/2010 | Ziemek | A61B 17/7055 606/71 |
| 2013/0172936 A1 * | 7/2013 | Berrevoets | A61B 17/7055 606/278 |

* cited by examiner

IMPLANT FOR IMMOBILIZING CERVICAL VERTEBRAE

CROSS-REFERENCE TO RELATED APPLICATIONS

This application is a continuation of U.S. application Ser. No. 14/596,849 filed on Jan. 14, 2015, which claims the benefit of and/or priority under 35 U.S.C. § 119(e) to U.S. Application No. 61/927,095 filed on Jan. 14, 2014 and titled "Implant For Immobilizing Cervical Vertebrae"; the entire contents of all of which are incorporated herein by reference.

FIELD OF INVENTION

The present disclosure relates to devices for immobilizing vertebrae of the spine and, more particularly, to devices for immobilizing the C1 vertebra with respect to the C2 vertebra of the spine.

BACKGROUND

Because of various circumstances such as injury, trauma, degeneration or the like, it becomes necessary to immobilize one or more vertebrae with respect to other vertebrae of the spine. This includes vertebrae of the lumbar, thoracic and the cervical areas. Various devices have been devised in order to accomplish this result.

While these devices are adequate to immobilize lumbar vertebrae, thoracic vertebrae, and some of the cervical vertebrae of the spine, they are particularly deficient in effectively immobilizing the C1 cervical vertebra relative to the C2 cervical vertebra. The C1 or atlas vertebra is the topmost cervical vertebra of the human spine and, along with the C2 or axis vertebra forms the joint connecting the skull and spine. A major difference of the atlas cervical vertebra relative to other vertebrae is that it does not have a body but is fused with the C2 vertebra. The C2 vertebra forms the pivot upon which C1 rotates. It is because of these peculiarities that prior art vertebral immobilization devices are inadequate for use with a C1 to C2 immobilization.

In view of the above, it can be appreciated that it would be desirable to have a better device, method and manner of immobilizing the C1 vertebra to the C2 vertebra.

The present invention sufficiently accomplishes these means.

SUMMARY OF THE INVENTION

The present invention is a spinal implant for immobilizing the C1 vertebra with respect to the C2 vertebra of the spine. The immobilization implant provides controlled coupling between the C1 and C2 vertebrae.

The immobilization implant includes a C1 component configured for attachment to the C1 vertebra, two C2 components each configured for attachment to the C2 vertebra, and a transverse element.

The C1 component can have a singular hook configured for placement midline on the C1 vertebra or multiple hooks configured for placement on multiple areas of the C1 vertebra. The arms and/or hook(s) are capable of being bent and translated to a desired position. The C1 component has two arms that each retains a rod holder which is configured to rotate and translate with respect to its respective arm for capturing a rod from each C2 component. This allows the device to accommodate varying anatomy.

In one form, the rod holder of each arm is retained in a slot in the upper surface of the respective arm. This allows each rod holder to translate along the respective arm in the cephalad-caudal direction. Rotation of each rod holder is fixed through interaction between structures on the bottom outside surface of the rod holder and structures beneath the bottom outside surface of the rod holder within the slot. In a particular instance, and without being limiting, such structures may be serrations, teeth or the like. Downward pressure exerted on the rod holder causes the two structures to mesh and lock. Other manners of fixing rotation of the rod holder may be used.

In another form, the rod holder of each arm is retained in a slot in the side surface of the respective arm. This allows each rod holder to translate along the respective side arm in the cephalad-caudal direction. Rotation of each rod holder is fixed through interaction between structures on the lower outside surface of the rod holder and structures adjacent the lower outside surface of the rod holder within the slot. In a particular instance, and without being limiting, such structures may be serrations, teeth or the like. Downward pressure exerted on the rod holder causes the two structures to mesh and lock. Other manners of fixing rotation of the rod holder may be used.

The underside of the C1 hook may be configured to provide stable securing of the C1 hook at its implanted position after the surgeon releases the implant instrumentation therefrom. This feature may be embodied as spring-loaded serrated teeth that projects from the C1 hook. The serrated teeth are angled and thus retained within the hook such that the serrated teeth recess into the hook during insertion and positioning of the C1 hook on the lamina of (or other relevant anatomy) at the particular level (e.g. C1), then is biased against the lamina of (or other relevant anatomy) by its spring-loading to help keep the hook in the same position at which it was intended.

Each C2 component has a body with a hook for connection with a side of the C2 vertebra lamina and a rod for attachment to one of the rod holders of the C1 component. Each C2 component is also configured to receive and secure the transverse connector or element that holds a position of the C2 components relative to one another. The transverse element runs caudally to the C2 spinous process. In one form, the body of each C2 component is integrated with a plate that is configured to be compressed against the C2 vertebra spinous process. Each plate includes projecting spikes to aid in preventing migration of the construct once installed.

In one form, the transverse element may include integrated connectors configured to connect the C1/C2 construct (the present spinal implant) to an occipital rod that connects the occiput to the cervical/thoracic region.

The present spinal implant may also be used with respect to the immobilization of vertebrae other than the C1/C2 vertebrae such as the other cervical vertebrae, the thoracic vertebrae, and the lumbar vertebrae.

BRIEF DESCRIPTION OF THE DRAWINGS

The above mentioned and other features of this invention, and the manner of attaining them, will become apparent and the invention itself will be better understood by reference to the following description of embodiments of the invention taken in conjunction with the accompanying drawings, wherein.

Although the drawings represent embodiments of various features and components according to the present invention, the drawings are not necessarily to scale and certain features may be enhanced in order to better illustrate and explain the present invention. The exemplifications set out herein thus illustrate embodiments of the invention, and such exemplifications are not to be construed as limiting the scope of the invention in any manner.

DETAILED DESCRIPTION

Those of skill in the art will understand that various details of the invention may be changed without departing from the spirit and scope of the invention. Furthermore, the foregoing description is for illustration only, and not for the purpose of limitation.

Figure 1:
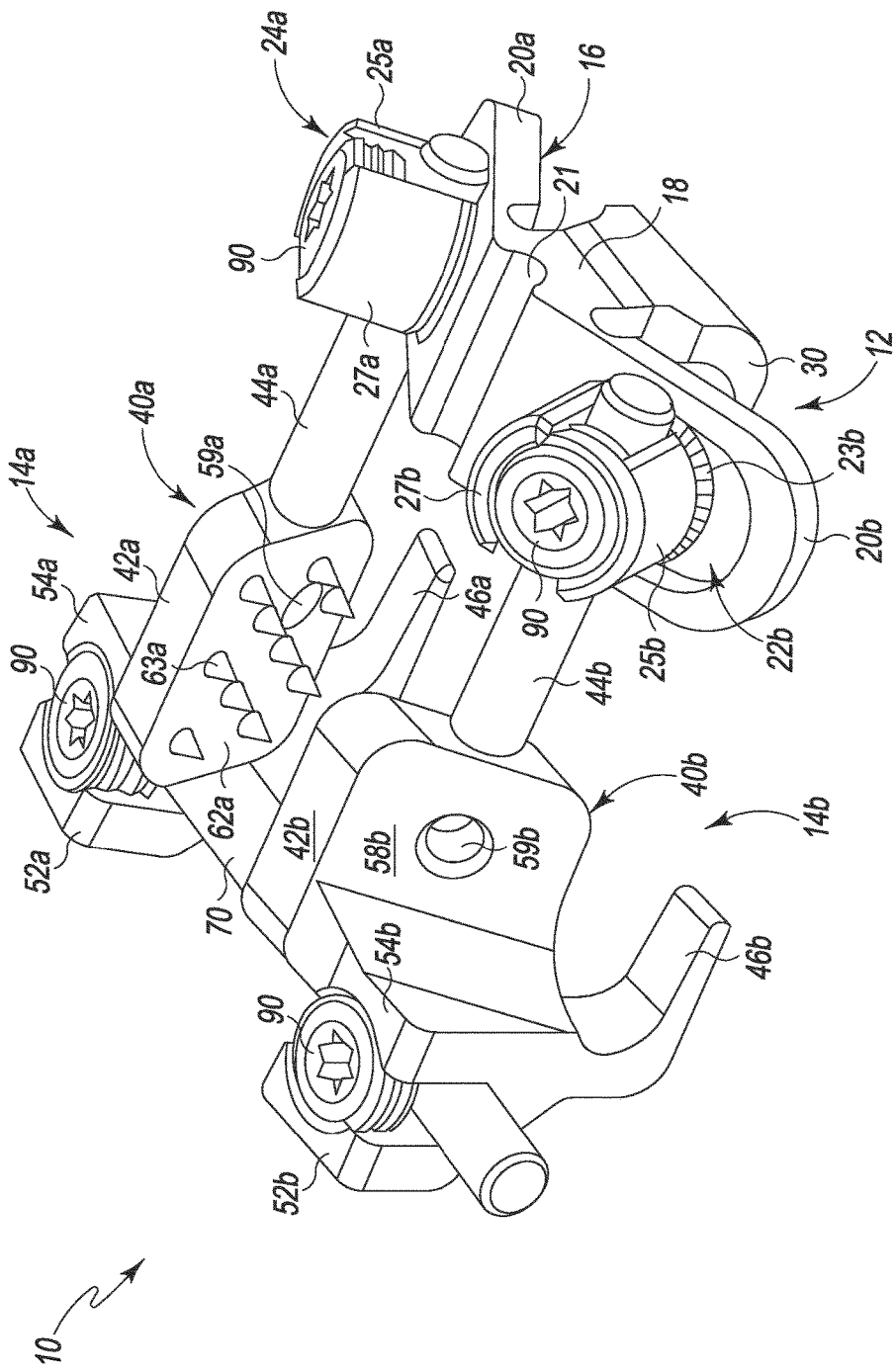
FIG. 1 is a view of a device for immobilizing a C1 vertebra of the spine relative to a C2 vertebra of the spine fashioned in accordance with the principles of the present invention.

Referring to the figures and in particular, FIG. 1, there is depicted an exemplary embodiment of an implant or device, generally designated 10, for immobilizing vertebrae of the spine and particularly, but not necessarily, the cervical vertebrae of the spine and, more particularly, but not necessarily, a C1 (atlas) vertebra of the spine relative to a C2 (axis) vertebra of the spine fashioned in accordance with the present principles. Thus, while the present vertebral immobilization implant 10 is shown and described herein with respect to the C1 and C2 vertebrae of the spine, it should be appreciated that the vertebral immobilization implant 10 may be used with other vertebrae of the spine. Additionally, as described further below, the vertebral immobilization implant 10 allows connection to other vertebral implants if desired.

As seen in FIG. 1, in general, the vertebral immobilization implant 10 has a C1 component 12 configured to attach to the C1 vertebra, and two C2 components 14a, 14b each one configured to attach to the C2 vertebra. Particularly, the C1 component 12 is attached to the posterior arch of the C1 vertebra, while each C2 component 14a, 14b attaches to the vertebral body of C2 on opposite sides of its spinous process (see, e.g. FIGS. 8-10). A transverse element or connector, shown in the form of a rod 70, is provided between and captured by the two C2 components 14a, 14b. The transverse element 70 allows the position of the C2 components to be fixed relative to one another and to aid in securing each C2 component by compression to respective sides of the C2 spinous process.

Figure 4:
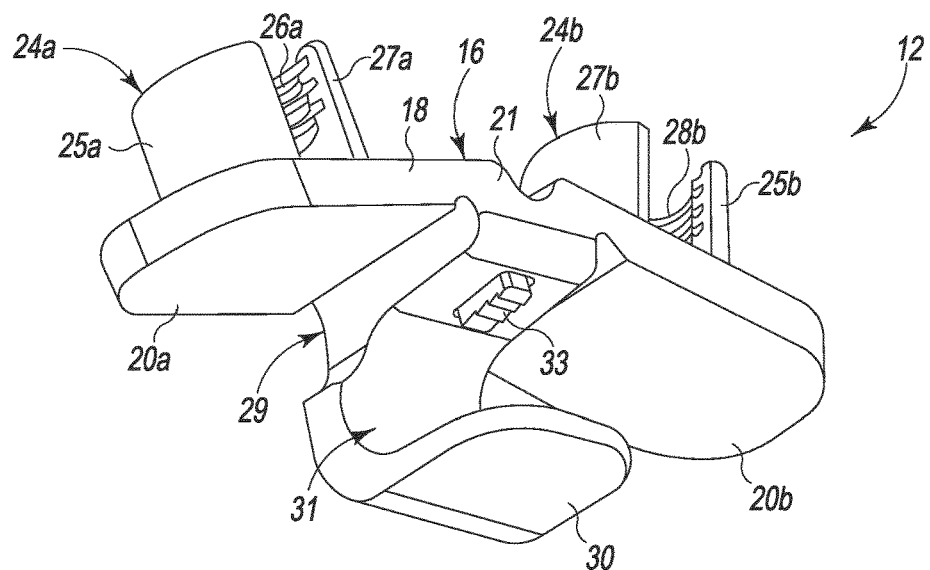
FIG. 4 is a view of a C1 component of the cervical vertebrae immobilization device of FIG. 1.
Figure 6:
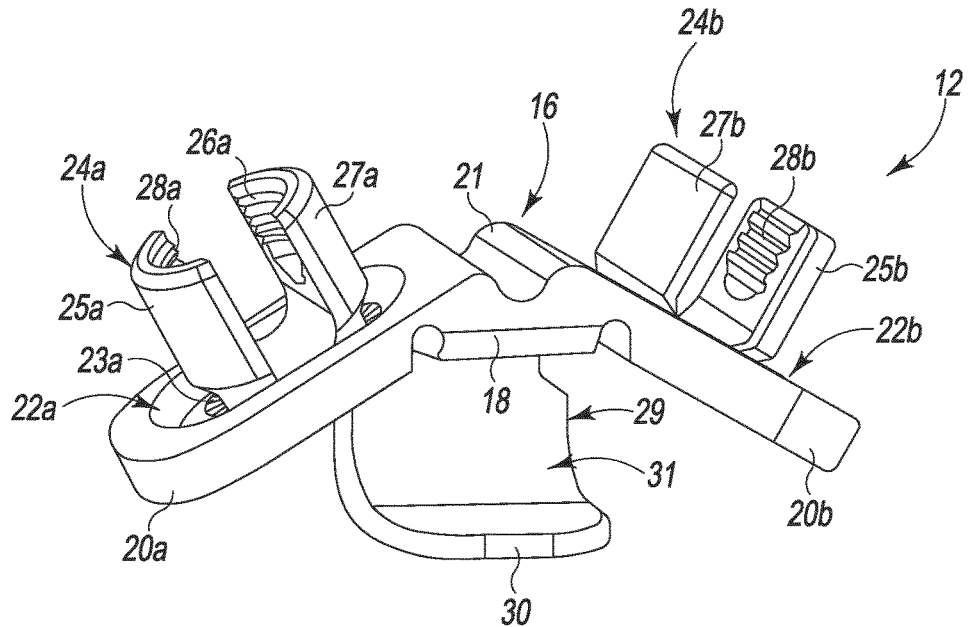
FIG. 6 is another view of the C1 component of FIG. 4.
Figure 7:
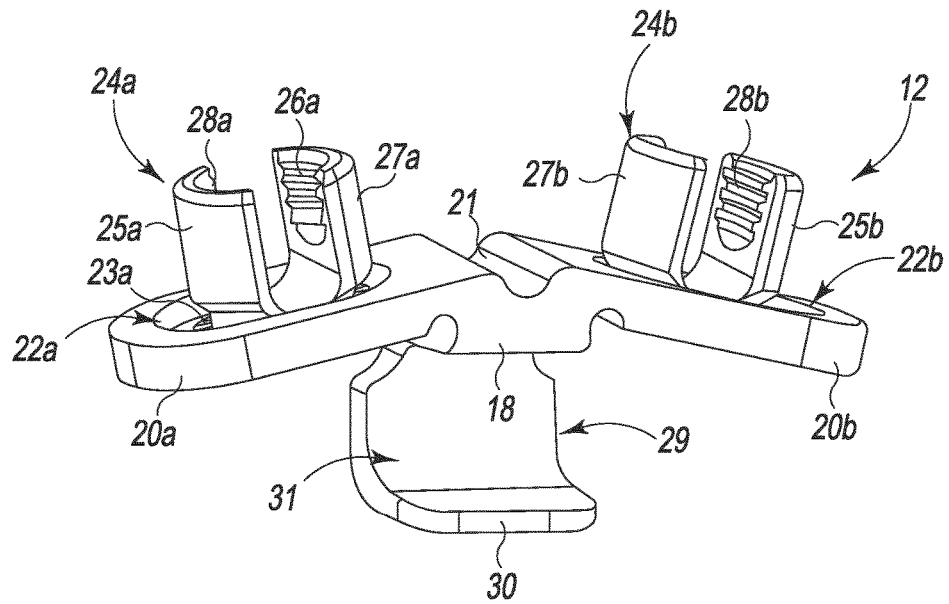
FIG. 7 is another view of the C1 component of FIG. 4.

FIG. 4 shows the C1 component 12. The C1 component 12 is made from a biocompatible material such as, but not limited to, stainless steel or titanium. The C1 component 12 is defined by a body 16 having first and second arms, wings, extensions or the like (arms) 20a, 20b that project from a generally central head 18, the nomenclature first and second being arbitrary here and throughout unless otherwise indicated. Each arm 20a, 20b is generally paddle or ovoid-shaped but may take different forms if desired. A channel, groove, concavity, depression or the like 21 separates the first and second arms 20a, 20b. As depicted in FIG. 4, each arm 20a, 20b project outwardly and generally downward. Each arm however, may be angled as desired relative to the head 18. This is particularly illustrated in the position of the arms 20a, 20b in FIGS. 6 and 7. Angling the arms 20a, 20b provides a better fit on the C1 vertebra.

Referring back to FIG. 4, the first arm 20a includes a recess, cutout or the like (recess) 22a that extends in and along an upper surface of the arm 20a. A first holder 24a is positioned within the recess 22a. The first holder 24a is rotatable within the recess 22a and thus relative to the arm 20a. The rotational position of the first holder 24a is fixed through interaction of the bottom area of the first holder 24a with a first fixation structure 23a within the recess 22a. The first fixation structure 23a is illustrated as a first ring of teeth, notches, serrations or the like (teeth) with the bottom area of the first holder 24a configured with a like ring of teeth. The first holder 24a may also translate within the recess 22a.

The first holder 24a is generally U-shaped and thus defines a slot between first and second cupped sides 25a, 27a. The slot of the first holder 24a is configured to receive a bar or rod 44a of the C2 component 14a. The first side 25a has threading 28a on the inside cupped surface thereof, with the second side 27a also having threading 26a on the inside surface thereof. The internal threading 26a, 28a is configured to receive a threaded set screw 90 for securing the bar 44a of the C2 component.

The second arm 20b includes a recess, cutout or the like (recess) 22b that extends in and along an upper surface of the arm 20b. A second holder 24b is positioned within the recess 22b. The second holder 24b is rotatable within the recess 22b and thus relative to the arm 20b. The rotational position of the second holder 24b is fixed through interaction of the bottom area of the second holder 24b with a second fixation structure 23b within the recess 22b. The second fixation structure 23b is illustrated as a second ring of teeth, notches, serrations or the like (teeth) with the bottom area of the second holder 24b configured with a like ring of teeth. The second holder 24b may also translate within the recess 22b.

The second holder 24b is generally U-shaped and thus defines a slot between first and second cupped sides 25b, 27b. The slot of the second holder 24b is configured to receive a bar or rod 44b of the C2 component 14b. The first side 25b has threading 28b on the inside cupped surface thereof, with the second side 27b also having threading 26b on the inside surface thereof. The internal threading 26b, 28b is configured to receive a threaded set screw 90 for securing the bar 44b of the C2 component.

Figure 5:
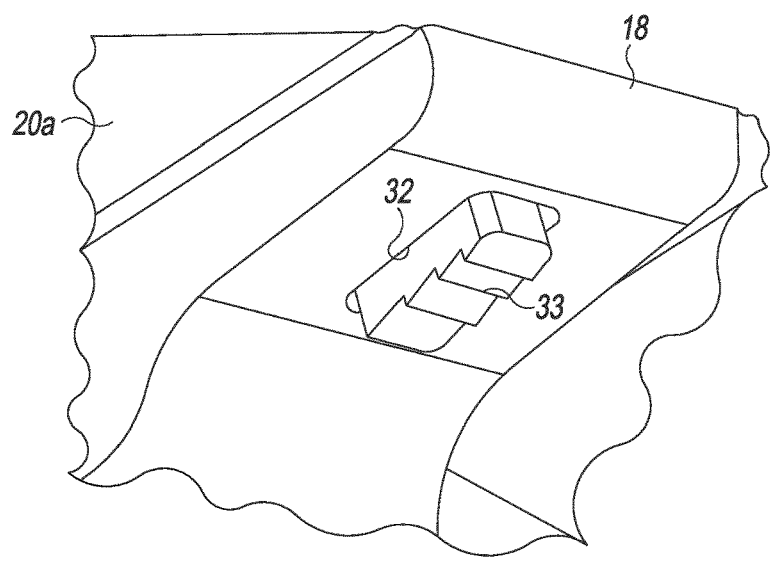
FIG. 5 is an enlarged partial view of the C1 component of FIG. 4.

As seen in FIGS. 4 and 5, the C1 component 12 has a hook structure 29 extending from the underside of the head 18. The hook 29 has a generally planar tongue 30 that defines a recess 31. The hook 29 is configured to attach to and around the posterior arch of the C1 vertebra and, particularly, the posterior arch of the C1 vertebra is received in the recess 31 of the hook 29 with the tongue extending under the C1 posterior arch, and more particularly midline on the C1 vertebra. The hook 29 is configured to be bent at various angles to accommodate varying C1 anatomy.

The underside of the hook 29 is configured to provide stable securement of the hook 29 at its implanted position after it is released from the implant instrumentation. While not being limiting, in one form, this feature is embodied as spring-loaded serrated teeth 33 that projects from a recess 32 on the underside of the hook 29. The serrated teeth 33 are angled and thus retained within the recess 32 such that the serrated teeth 33 recede into the head 18 during insertion and positioning of the hook 29 on the lamina of the C1 vertebra. The teeth 33 are then biased against the lamina of by its spring-loading in order to help keep the hook in the same position at which it was intended.

Figure 2:
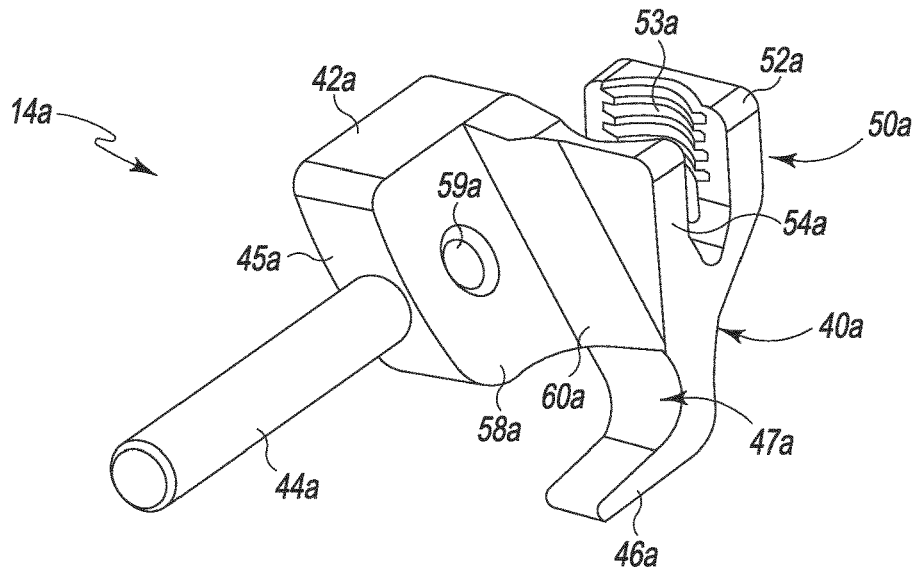
FIG. 2 is a view of one of two C2 components of the cervical vertebrae immobilization device of FIG. 1.
Figure 3:
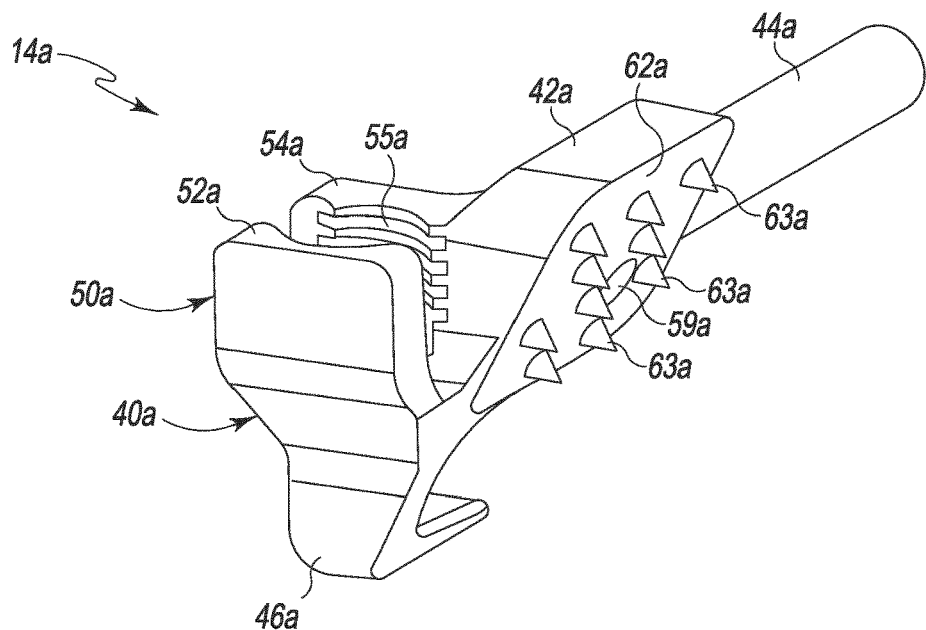
FIG. 3 is another view of the C2 component of FIG. 2.

FIGS. 2 and 3 particularly show the first C2 component 14a. The second C2 component 14b is a mirror image of the first C2 component. As such the second C2 component will not be discussed in detail since its features, components and configuration are the same as the first C2 component, the numerical labeling of which ends in a "b". The first C2 component 14a has a body 40a that defines a plate 42a having an angled front face 58a and an angled rear face 62a, the nomenclature front and rear being arbitrary. The front face 58a is generally planar. The rear face 62a is generally planar with a plurality of spikes, projections or the like (spikes) 63a extending outwardly therefrom. The rear face 68a is angled to follow the contour or angling of a side of the spinous process SP (see, e.g., FIGS. 8-10). The spikes 63a are configured to grip the side of the spinous process SP. A bore 59a extends through the plate 42a from the front face 58a to the rear face 68a. The bore 59a accepts a bone screw or other fastener (not shown) in order to positively secure the plate 42a to the side of the spinous process SP if desired.

The body 40a further has a rod, shaft, pole or the like (rod) 44a that projects outwardly from a side 45a of the plate 42a. The rod 44a is configured to be received in the first holder 24a of the C1 component (see, e.g., FIGS. 8-10). The rod 44a also has a length that allows the first holder 24a of the C1 component to receive and retain the rod 44a at various longitudinal positions along the rod, thereby providing length adjustment between the C1 component/C1 vertebra and the first C2 component/C2 vertebra and/or a side of the spinous process SP. This accommodates variations in anatomy (i.e. spacing between the C1 vertebra and the C2 vertebra).

The body 40a moreover has a rod holder 50a that extends from an end of the plate 42a opposite the end 45a and offset from a longitudinal axis of the rod 44a. The rod holder 50a has a front portion 54a that extends outward from and generally perpendicular to the side of the plate 42a. The front portion 54a has threading 55a on an inside surface. The rod holder 50a further includes a rear portion 52a that extends from the bottom of the front portion 54a such that the rod holder 50a is generally cupped shaped and defines a rod holder area therein and between the front and rear portions 54a, 52a. The rear portion 52a has threading 53a on an inside surface facing the threading 55a of the front portion 54a. The threading 53a, 55a is configured to receive a set screw 90 or the like (see, e.g., FIGS. 8-10).

A hook 46a extends from a bottom of the rod holder 50a and defines a hook area 47a. The hook 46a is configured to attach onto and extend under a portion of the lamina of the C2 vertebra adjacent one side (first side) of the spinous process SP thereof (see, e.g. FIGS. 8-10). Particularly, as discerned in FIGS. 8-10, the first C2 component 14a is designed to hook or grasp onto and/or around the inferior end of the C2 lamina.

As indicated above, the second C2 component 14b is a mirror configuration of the C1 component 14a. Thus, while the first C2 component 14a is configured to connect to the left side of the C2 vertebra and extend to the left side of the C1 vertebra, the second C2 component 14b is configured to connect to the right side of the C2 vertebra and extend to the right side of the C1 vertebra. The rod 44a of the first C2 component 14a is received in the rod holder 24a of the C1 component 12 while the rod 44b of the second C2 component 14b is received in the rod holder 24b of the C1 component.

Figure 8:
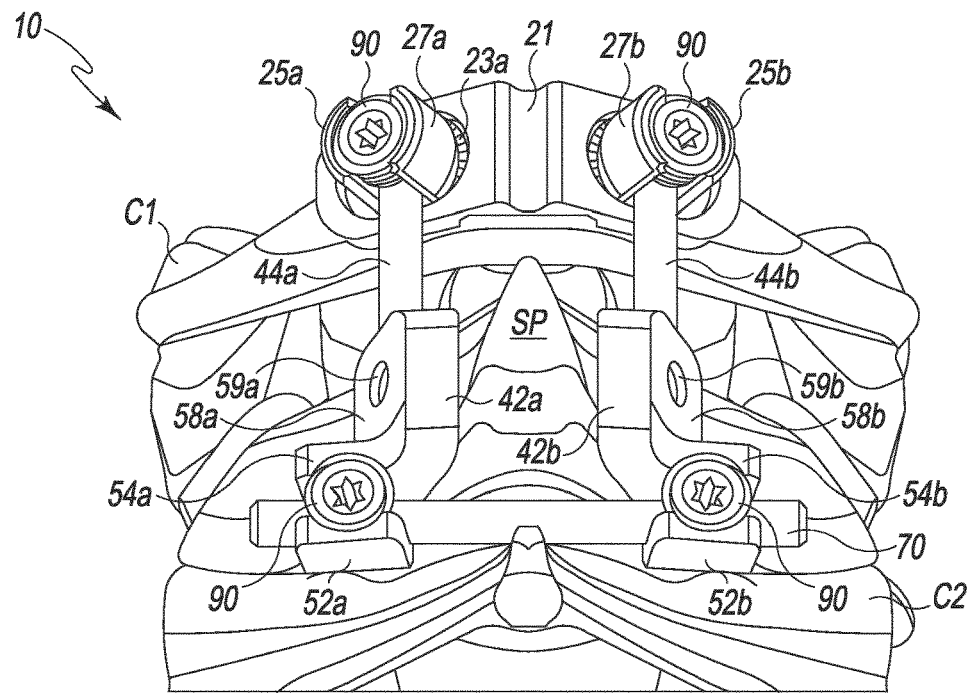
FIG. 8 is a view of the cervical vertebrae immobilization device of FIG. 1 installed on the C1 and C2 vertebrae of the spine.
Figure 9:
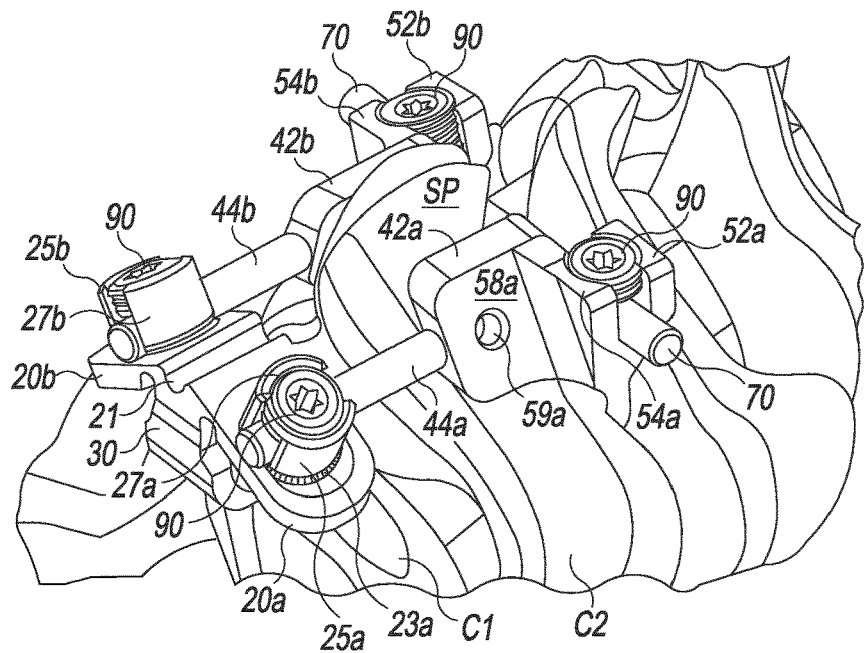
FIG. 9 is another view of the cervical vertebrae immobilization device of FIG. 1 installed on the C1 and C2 vertebrae of the spine.

FIGS. 8 and 9 particularly show various views of the present vertebral immobilization implant 10 situated, implanted on, or otherwise attached to and between the C1 vertebra and the C2 vertebra. The vertebral immobilization implant 10 stabilizes the C1 and C2 vertebrae relative to one another.

Figure 10:
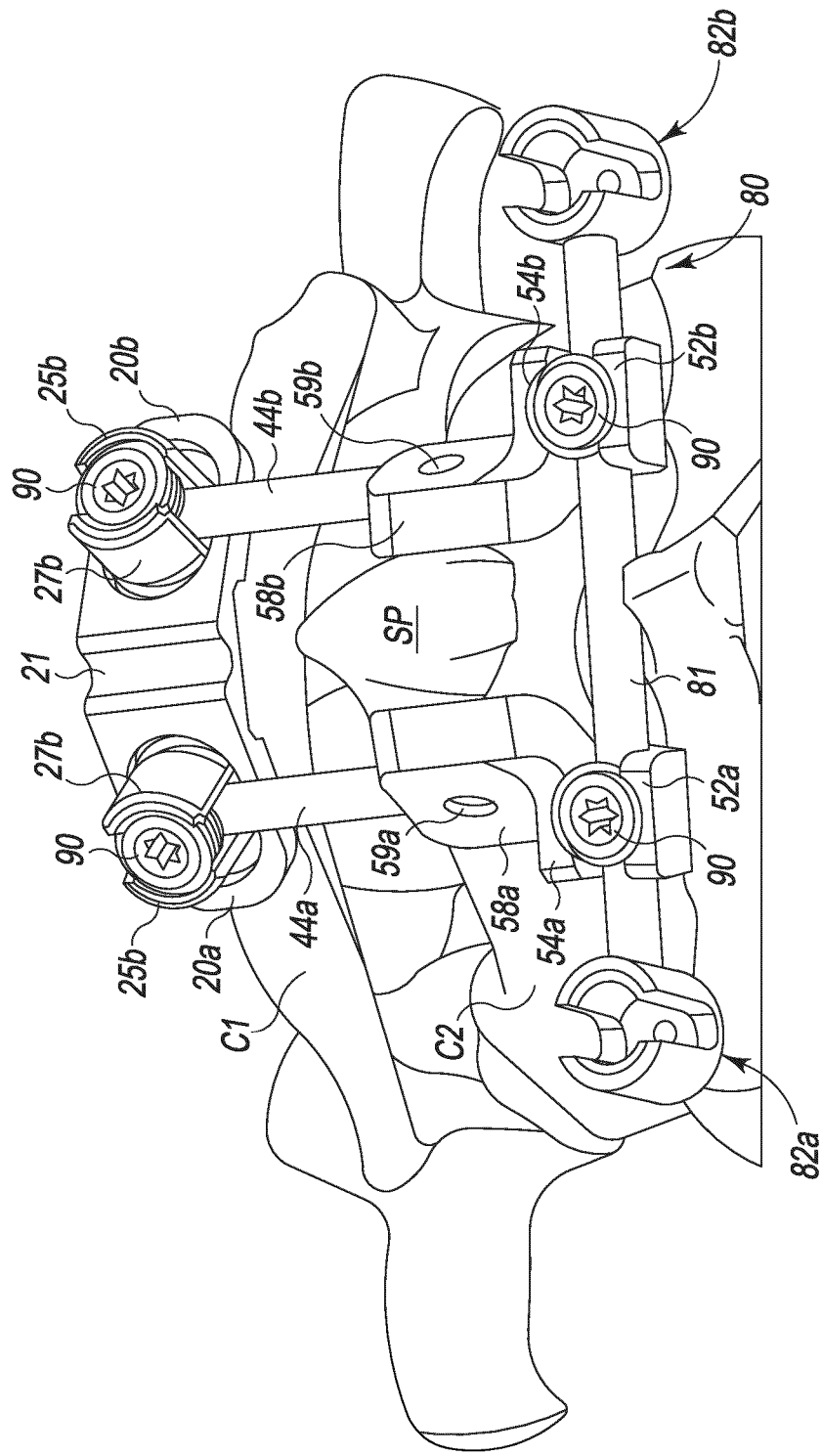
FIG. 10 is a view of the cervical vertebrae immobilization device of FIG. 1 installed on the C1 and C2 vertebrae of the spine and having an additional transverse element thereon for connecting the cervical immobilization device to an occipital rod.

FIG. 10 shows a variation of the present implant 10 wherein the transverse element 70 has been replace with a transverse element assembly 80 for connecting the present implant 10 to one or more occipital rods that connect the occiput to the cervical/thoracic region of the spine. The transverse element assembly 80 includes a rod 81 that is configured to be received in the first and second rod holders 50a, 50b of the respective first and second C2 components 14a, 14b. A first rod holder (integrated connector) 82a is provided on a first end of the rod 81 and is configured to receive a connecting rod (not shown). A second rod holder (integrated connector) 82b is provided on a second end of the rod 81 and is configured to receive another connecting rod (not shown). The rod holders 82a, 82b are configured to each receive a threaded set screw 90. Other configurations and/or manners of providing this connection are contemplated.

Referring to FIGS. 11-16, there is shown another exemplary embodiment of an implant or device, generally designated 100, for immobilizing vertebrae of the spine in like manner and function and to the implant 10. In general, the vertebral immobilization implant 100 has a C1 component 112 configured to attach to the C1 vertebra, and two C2 components 114a, 114b each one configured to attach to the C2 vertebra. Particularly, the C1 component is attached to the posterior arch of the C1 vertebra, while each C2 component 114a, 114b attaches to the vertebral body of C2, preferably, but not necessarily, on opposite sides of its spinous process (see, e.g. FIGS. 8-10). A transverse element or connector, shown in the form of a rod 170, is provided between and captured by the two C2 components 114a, 114b. The transverse element 170 allows the position of the C2 components 114a, 114b to be fixed relative to one another and to aid in securing each C2 component by compression to respective sides of the C2 spinous process.

The C1 component 112 is made from a biocompatible material such as, but not limited to, stainless steel or titanium. The C1 component 112 is defined by a body 116 having first and second arms, wings, extensions or the like (arms) 117a, 117b, the nomenclature first and second being arbitrary here and throughout unless otherwise indicated. Each arm 117a, 117b is generally paddle or ovoid-shaped but may take different forms if desired. A lower notch 118a is formed at the bottom of the body 116 between the first and second arms 117a, 117b. A first upper notch is formed at the top of the body 116 adjacent the first arm 117a, while a second upper notch is formed at the top of the body 116 adjacent the second arm 117b. Each arm 117a, 117b project outwardly and generally downward. Each arm however, may be angled as desired relative to the head 18.

Figure 11:
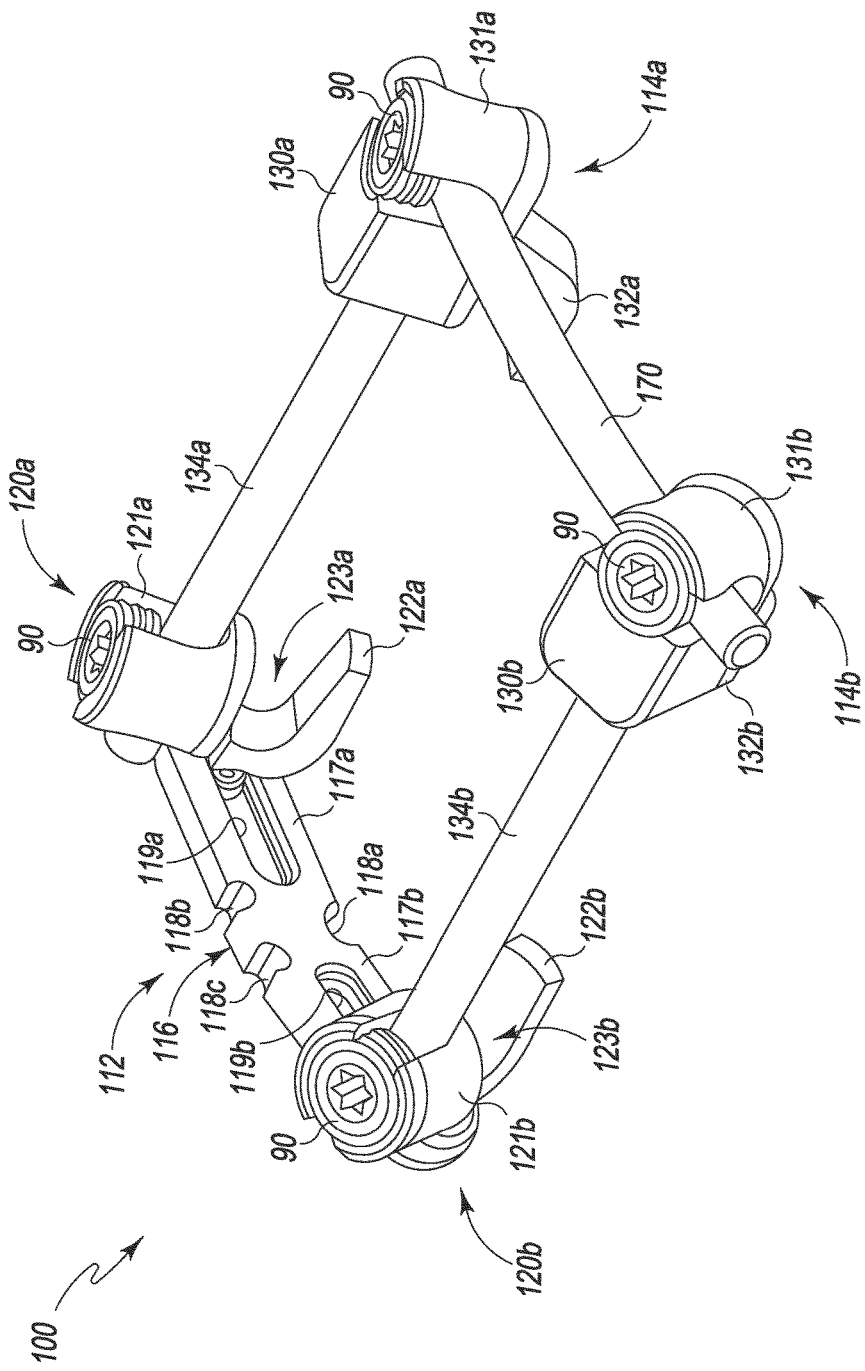
FIG. 11 is a view of another cervical vertebrae immobilization device fashioned in accordance with the principles of the present invention.
Figure 12:
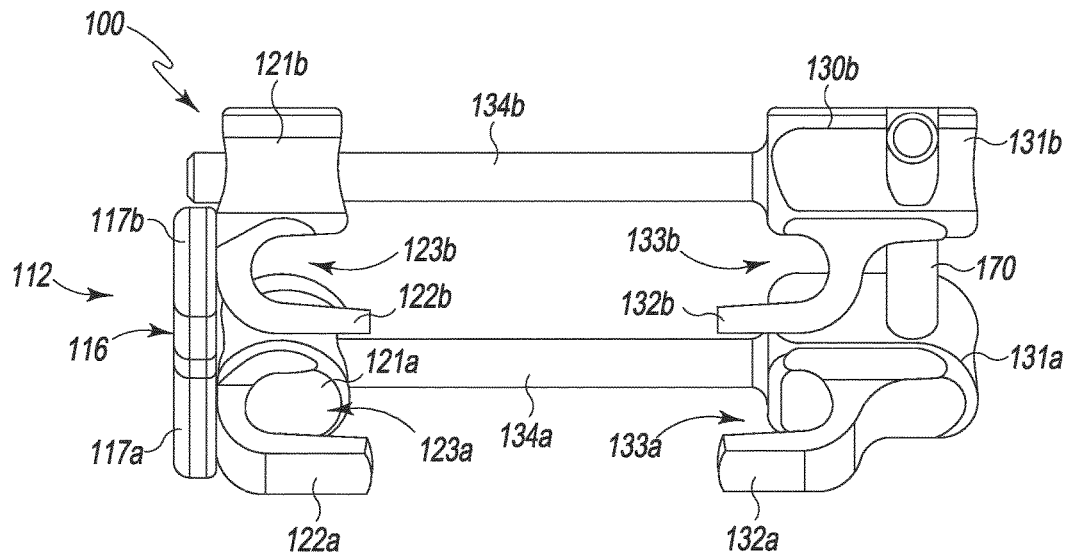
FIG. 12 is an underside view of the cervical vertebrae immobilization device of FIG. 11.
Figure 13:
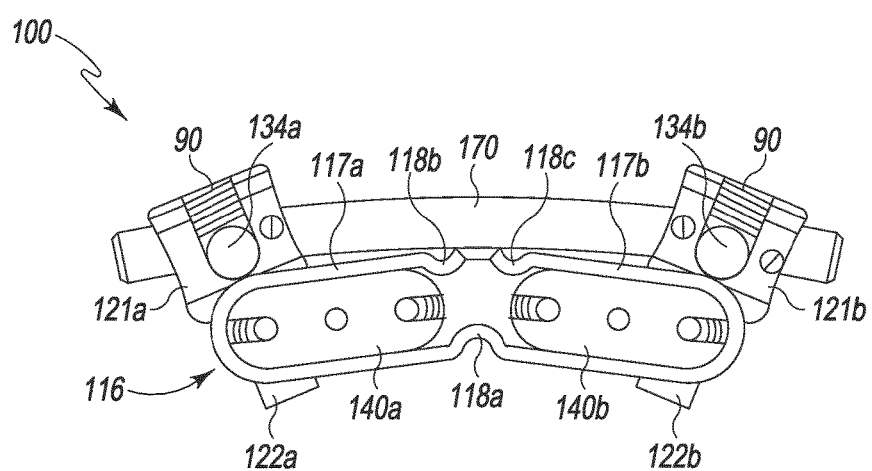
FIG. 13 is an end view of the cervical vertebrae immobilization device of FIG. 11.
Figure 14:
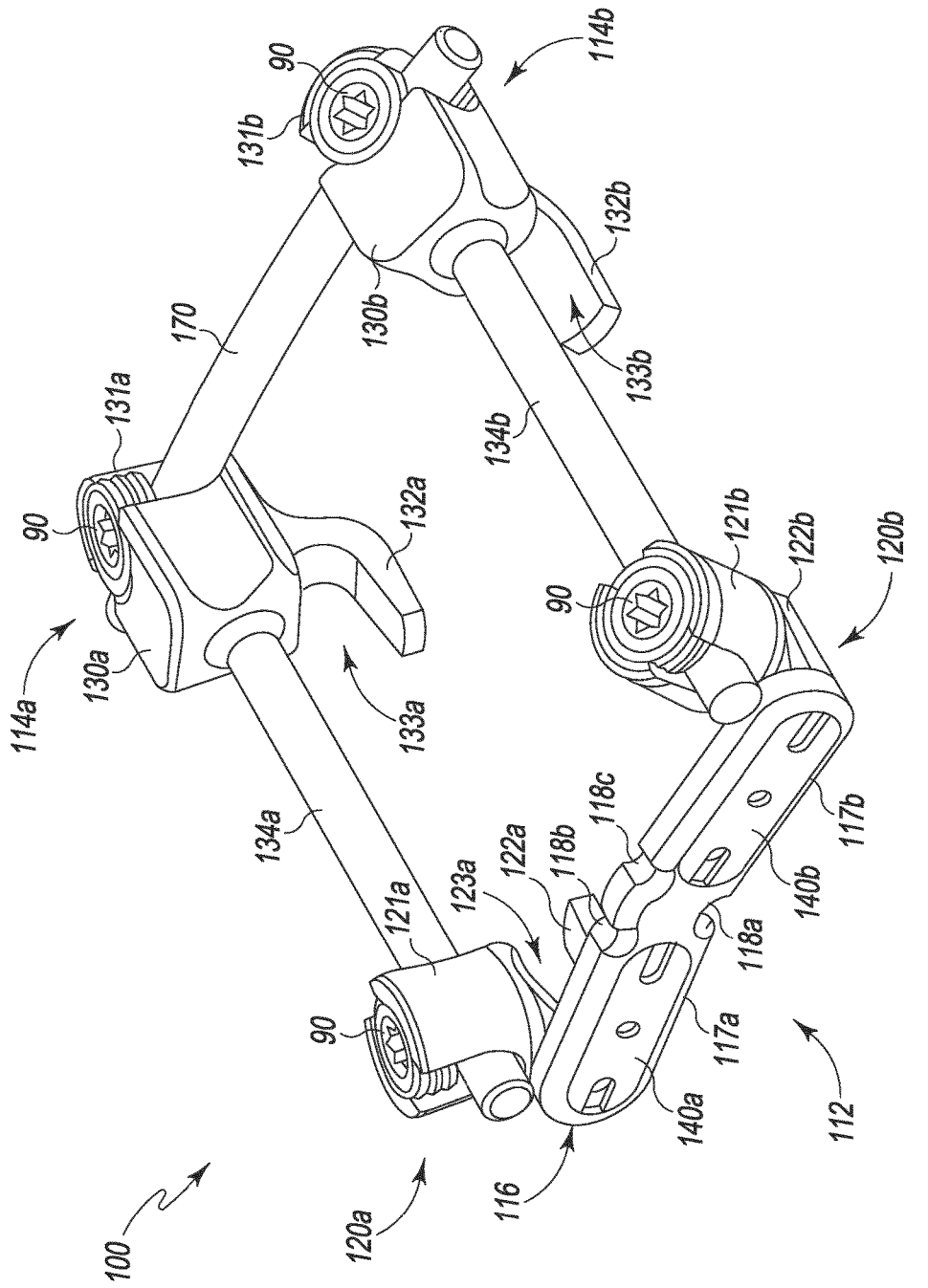
FIG. 14 is another view of the cervical vertebrae immobilization device of FIG. 11.
Figure 15:
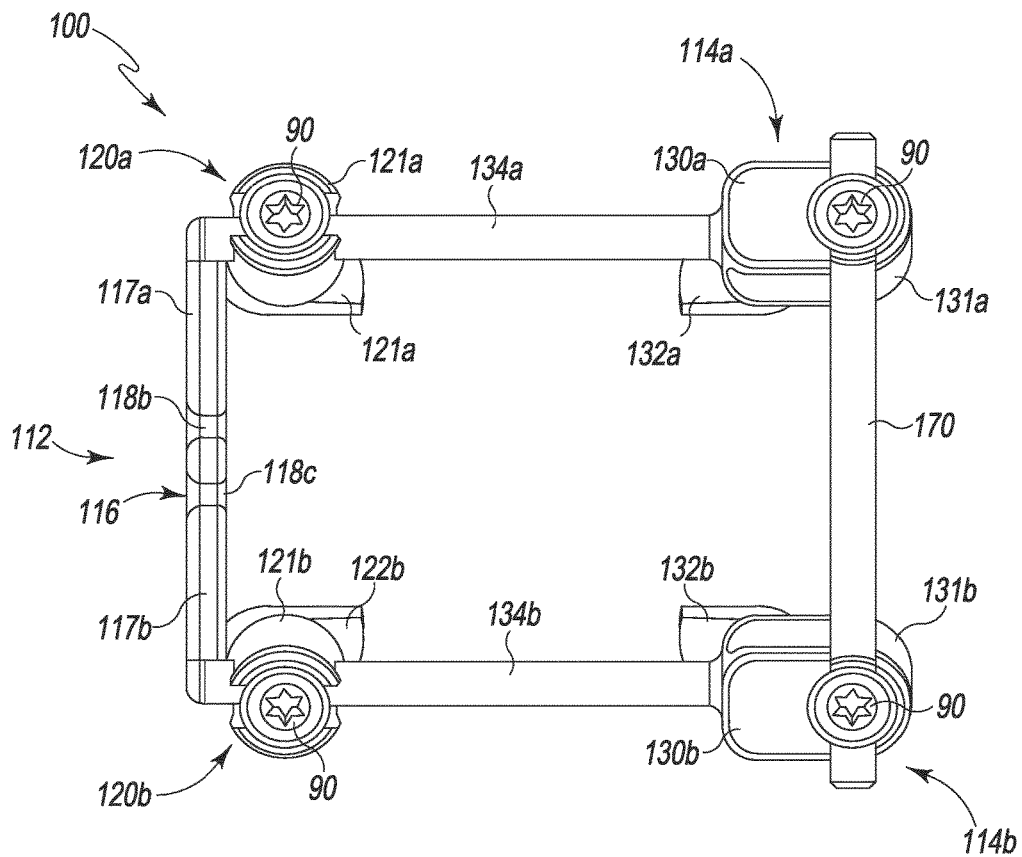
FIG. 15 is a top view of the cervical vertebrae immobilization device of FIG. 11.
Figure 16:
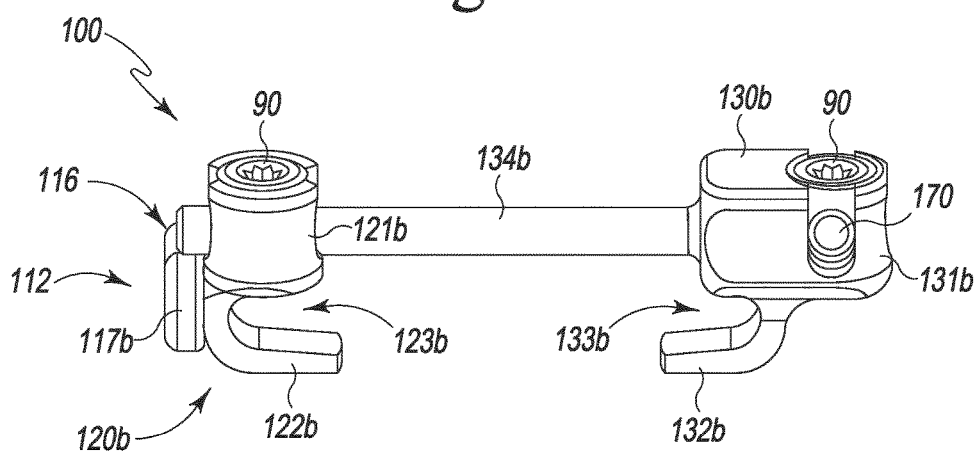
FIG. 16 is an end view of the cervical vertebrae immobilization device of FIG. 11.

As best seen in FIG. 11, the first arm 117a includes a slot or the like 119a that extends in and along the side of the first arm 117a. A first adjustable element 120a is retained in the slot 119a so as to be translatable (movable) along the length of the slot 119a (in the medial-lateral direction or transverse plane) and rotatable relative thereto. As such, the first adjustable element 120a is rotatable relative to the first arm 117a. A weld plate 140a ensures that a hook 121a of the first adjustable element 120a does not disassociate from the body 116/arm 117a. The weld plate 120a also ensures that the translation of the first adjustable element remains parallel with the medial-lateral (transverse) plane and does not travel obliquely.

The first adjustable element 120a includes a generally U-shaped rod holder 121a defining a slot between two cupped sides, the slot configured to receive the rod (134a, 134b) of a C2 component (114a, 114b). While not seen, the two cupped sides have threading on the inside cupped surface thereof. The internal threading is configured to receive a threaded set screw 90 for securing the rod of the C2 component.

The first adjustable element 120a also includes a hook 122a extending from the underside of the rod holder 121a. The hook 122a defines a pocket or reception area 123a configured to attach to and around a portion of the posterior arch of the C1 vertebra. The hook 122a may be configured to be bent at various angles to accommodate varying C1 vertebra anatomy.

Again, as best seen in FIG. 11, the second arm 117b includes a slot or the like 119b that extends in and along the side of the second arm 117b. A second adjustable element 120b is retained in the slot 119b so as to be translatable (movable) along the length of the slot 119b (in the medial-lateral direction or transverse plane) and rotatable relative thereto. As such, the second adjustable element 120b is rotatable relative to the second arm 117b. A weld plate 140b ensures that a hook 121b of the second adjustable element 120b does not disassociate from the body 116/arm 117b. The weld plate 120b also ensures that the translation of the first adjustable element remains parallel with the medial-lateral (transverse) plane and does not travel obliquely.

The second adjustable element 120b includes a generally U-shaped rod holder 121b defining a slot between two cupped sides, the slot configured to receive the rod (134a, 134b) of a C2 component (114a, 114b). While not seen, the two cupped sides have threading on the inside cupped surface thereof. The internal threading is configured to receive a threaded set screw 90 for securing the rod of a C2 component.

The second adjustable element 120b also includes a hook 122b extending from the underside of the rod holder 121b. The hook 122b defines a pocket or reception area 123b configured to attach to and around a portion of the posterior arch of the C1 vertebra. The hook 122b may be configured to be bent at various angles to accommodate varying C1 vertebra anatomy.

The C2 component 114a will now be described. The second C2 component 114b is a mirror image of the first C2 component 114a. As such the second C2 component 114b will not be discussed in detail since its features, components and configuration are the same as the first C2 component, and its numerical labeling of which ends in a "b". The first C2 component 114a has a body 130a having a rod, shaft, pole or the like (rod) 134a that projects outwardly from an end of the body 130a. The rod 134a is configured to be received in the rod holder 121a of the C1 component. The rod 134a also has a length that allows the rod holder 121a of the C1 component to receive and retain the rod 134a at various longitudinal positions along the rod, thereby providing length adjustment between the C1 component/C1 vertebra and the first C2 component/C2 vertebra. This accommodates variations in anatomy (i.e. spacing between the C1 vertebra and the C2 vertebra).

The body 130a moreover has a rod holder 131a that is formed at an end of the body 130a opposite the rod 134a. The rod holder 131a utilizes an end wall of the body 130a as one side of the two sided rod holder 131a and a shaped flange as the other side. The outside surface of the end wall and the inside surface of the shaped flange both have threading for receiving the threaded set screw 90. A hook 132a extends from a bottom of the rod holder 131a and defines a hook area 133a (see, e.g., FIG. 12). The hook 131a is configured to attach onto and extend under a portion of the lamina of the C2 vertebra adjacent one side of its spinous process SP. This is in like manner to the first C2 component 14a shown in FIGS. 8-10 wherein the first C2 component 14a is designed to hook or grasp onto and/or around the inferior end of the C2 lamina.

As indicated above, the second C2 component 114b is a mirror configuration of the C1 component 114a. Thus, while the first C2 component 114a is configured to connect to the left side of the C2 vertebra and extend to the left side of the C1 vertebra, the second C2 component 114b is configured to connect to the right side of the C2 vertebra and extend to the right side of the C1 vertebra. The rod 44a of the first C2 component 114a is received in the rod holder 24a of the C1 component 12 while the rod 44b of the second C2 component 114b is received in the rod holder 24b of the C1 component.

The implant 100 is attached to the spine in a manner similar if not the same as the implant 10. As such, reference should be made to FIGS. 8-10 that show various views of the vertebral immobilization implant 10 situated, implanted on, or otherwise attached to and between the C1 vertebra and the C2 vertebra. The vertebral immobilization implant 100 stabilizes the C1 and C2 vertebrae relative to one another.

While the invention has been illustrated and described in detail in the foregoing drawings and description, the same is to be considered as illustrative and not restrictive in character, it being understood that only illustrative embodiments thereof have been show and described and that all changes and modifications that are within the scope of the following claims are desired to be protected.

All references cited in this specification are incorporated herein by reference to the extent that they supplement, explain, provide a background for or teach methodology or techniques employed herein.

What is claimed is:

1. An implant for immobilizing a first vertebra relative to a second vertebra, the implant comprising:
   a first component having a hook for attachment to a posterior arch of the first vertebra, a right wing, a left wing, a right element holder situated on the right wing, and a left element holder situated on the left wing, the right element holder free to translate laterally along the right wing and translate rotationally with respect to the right wing, the left element holder free to translate laterally along the left wing and translate rotationally with respect to the left wing;
   a second component having a body configured to abut the second vertebra, a first rod holder extending from the body, and a first post extending from the body and configured to be received in the right element holder of the first component;
   a third component having a body configured to abut the second vertebra of the spine, a second rod holder extending from the body, and a second post extending from the body and configured to be received in the left element holder of the first component; and
   a rod configured to be received in and extend between the first rod holder of the second component and the second rod holder of the third component.

2. The implant of claim 1, wherein the body of the second component includes a plurality of projections extending therefrom to engage the second vertebra, and wherein the body of the third component includes a plurality of projections extending therefrom to engage the second vertebra.

3. The implant of claim 1, wherein the right wing extends along a right lateral side of the posterior arch of the first vertebra when the hook is attached to the posterior arch of the first vertebra, and wherein the left wing extends along a left lateral side of the posterior arch of the first vertebra when the hook is attached to the posterior arch of the first vertebra.

4. The implant of claim 1, further comprising a right element holder setscrew to fix in position and orientation of the right element holder relative to the right wing, and further comprising a left element holder setscrew to fix in position and orientation of the left element holder relative to the left wing.

5. The implant of claim 1, wherein the right and left wings of the body of the first component angle anteriorly from respective right and left sides of a hub of the body.

6. The implant of claim 5, wherein the hook of the first component extends from the hub.

7. The implant of claim 6, further comprising teeth disposed on an underside of the hub adjacent the hook.

8. The implant of claim 1, wherein the rod is retained in the first rod holder of the second component via a first rod holder setscrew, and in the second rod holder of the third component via a second rod holder setscrew.

9. The implant of claim 1, wherein the body of the second component has a bore extending from a face of the body through the body, and the body of the third component has a bore extending from a face of the body through the body.

10. A method of immobilizing a first vertebrae of a spine relative to a second vertebra of the spine comprising the steps of:

providing an implant for immobilizing the first vertebra of a spine relative to the second vertebra of the spine, the implant comprising:
      a first component having a hook for attachment to a portion of the first vertebra of a spine, a first wing, a second wing, a first element holder situated on the first wing, and a second element holder situated on the second wing, the first element holder free to translate laterally along the first wing and translate rotationally with respect to the first wing until fixed in position and orientation relative to the first wing, the second element holder free to translate laterally along the second wing and translate rotationally with respect to the second wing until fixed in position and orientation relative to the second wing;
      a second component having a body configured to abut a first lateral side of the second vertebra of the spine, a first rod holder extending from a first end of the body, and a first post extending from a second end of the body and configured to be received in the first element holder of the first component;
      a third component having a body configured to abut a second lateral side of the spinous process of the the second vertebra of the spine, a second rod holder extending from a first end of the body, and a second post extending from a second end of the body and configured to be received in the second element holder of the first component; and
      a rod configured to be received in and extend between the first rod holder of the second component and the second rod holder of the third component in order to fix position of the second and third components relative to one another and the spinous process of the second vertebra; and
   surgically installing the implant onto and between the first vertebra and the second vertebra of the spine.

11. The method of claim 10, wherein the step of providing the implant includes providing the implant with the first and second wings of a body of the first component angled anteriorly from respective first and second sides of a hub of the body.

12. The method of claim 11, wherein the step of providing the implant includes providing the hook of the first component to extend from the hub.

13. The method of claim 12, wherein the step of providing the implant includes providing teeth disposed on an underside of the hub adjacent the hook.

14. The method of claim 10, wherein the step of providing the implant includes providing a plurality of projections extending from the body of the second component to engage the second vertebra, and wherein the body of the third component includes a plurality of projections extending from the body of the third component to engage the second vertebra.

15. A spinal implant for immobilizing a first vertebra of a spine with respect to a second vertebra of the spine, the spinal implant comprising:
   a first component having a hub with a hook for attachment to the first vertebra of the spine extending anteriorly of the hub, a first wing that extends from a first side of the hub, a second wing that extends from a second side of the hub, a first element holder situated on the first wing, and a second element holder situated on the second wing, the first element holder free to translate laterally along the first wing and translate rotationally with respect to the first wing until fixed in position and orientation relative to the first wing, the second element holder free to translate laterally along the second wing and translate rotationally with respect to the second wing until fixed in position and orientation relative to the second wing;

a second component having a body that is configured to abut a spinous process of the second vertebra of the spine, a first rod holder extending from the body, and a first post extending from the body and configured to be received in the first element holder of the first component;

a third component having a body that is configured to abut the second vertebra of the spine, a second rod holder extending from the body, and a second post extending from the body and configured to be received in the second element holder of the first component; and a rod configured to be received in and extend between the first rod holder of the second component and the second rod holder of the third component in order to fix position of the second and third components relative to one another and the spinous process of the second vertebra; the implant providing controlled coupling between the first vertebra and the second vertebra.

16. The spinal implant of claim 15, wherein the first and second wings of the body of the first component angle anteriorly from the respective first and second sides of the hub of the body.

17. The spinal implant of claim 15, further comprising teeth disposed on an underside of the hub adjacent the hook.

18. The spinal implant of claim 15, wherein:
the rod comprises a cylindrical shape;
the first post comprises a cylindrical shape;
the second post comprises a cylindrical shape.

19. The spinal implant of claim 15, wherein the body of the second component includes a plurality of projections extending therefrom to engage the second vertebra, and wherein the body of the third component includes a plurality of projections extending therefrom to engage the second vertebra.

20. The spinal implant of claim 15, wherein the first wing includes a recess extending along an upper surface of the first wing to receive the first element holder, the second wing includes a recess extending along an upper surface of the second wing to receive the second element holder, wherein the first element holder includes teeth to engage serrations within the recess on the first wing to fix the rotational position of the first element holder, wherein the second element holder includes teeth to engage serrations within the recess on the second wing to fix the rotational position of the second element holder.

* * * * *